US010682472B2

(12) United States Patent
Wittland et al.

(10) Patent No.: US 10,682,472 B2
(45) Date of Patent: Jun. 16, 2020

(54) SAFETY DEVICE FOR PREFILLED SYRINGES, COMPRISING AN ANTI-TRIGGERING MECHANISM

(71) Applicants: Gerresheimer Regensburg GmbH, Regensburg (DE); Gerresheimer Bünde GmbH, Bünde (DE)

(72) Inventors: Frank Wittland, Enger (DE); Maximilian Vogl, Mantel (DE)

(73) Assignees: Gerresheimer Regensburg GmbH, Regensburg (DE); Gerresheimer Bünde GmbH, Bünde (DE)

(*) Notice: Subject to any disclaimer, the term of this patent is extended or adjusted under 35 U.S.C. 154(b) by 130 days.

(21) Appl. No.: 15/573,048

(22) PCT Filed: May 13, 2016

(86) PCT No.: PCT/EP2016/060857
§ 371 (c)(1),
(2) Date: Nov. 9, 2017

(87) PCT Pub. No.: WO2016/202510
PCT Pub. Date: Dec. 22, 2016

(65) Prior Publication Data
US 2018/0104421 A1 Apr. 19, 2018

(30) Foreign Application Priority Data
Jun. 15, 2015 (EP) .................. 15172166

(51) Int. Cl.
*A61M 5/32* (2006.01)
*A61M 5/00* (2006.01)
*A61M 5/31* (2006.01)

(52) U.S. Cl.
CPC .......... *A61M 5/3271* (2013.01); *A61M 5/008* (2013.01); *A61M 5/3202* (2013.01);
(Continued)

(58) Field of Classification Search
CPC ............... A61M 5/3272; A61M 5/326; A61M 2005/3267; A61M 5/3271
See application file for complete search history.

(56) References Cited

U.S. PATENT DOCUMENTS

| 5,429,612 A | 7/1995 | Berthier |
| 6,203,529 B1 | 3/2001 | Gabriel et al. |

(Continued)

FOREIGN PATENT DOCUMENTS

| CA | 2974585 | 8/2016 |
| CN | 101420995 A | 4/2009 |

(Continued)

OTHER PUBLICATIONS

Japanese Examination Report, dated Oct. 4, 2018, in Japanese Patent Application No. 2017-559507, a related application, 5 pp. (in Japanese language).

(Continued)

*Primary Examiner* — Nathan R Price
*Assistant Examiner* — Melissa A Snyder
(74) *Attorney, Agent, or Firm* — Leydig, Voit & Mayer, Ltd.

(57) ABSTRACT

Disclosed is a method for assembling a safety device and mounting the safety device on a syringe member before the syringe member is filled, said method comprising the steps of: providing a sleeve, a spring element and a mounting element; introducing the spring element into the sleeve along a mounting direction; introducing the mounting element into the sleeve along the mounting direction; obtaining the safety device; before the syringe body is filled, mounting the safety device on the syringe body by connecting the mounting element to the syringe body.

7 Claims, 8 Drawing Sheets

(52) U.S. Cl.
CPC .......... *A61M 5/326* (2013.01); *A61M 5/3257* (2013.01); *A61M 5/3269* (2013.01); *A61M 2005/3107* (2013.01); *A61M 2005/3267* (2013.01)

(56) References Cited

U.S. PATENT DOCUMENTS

| | | | |
|---|---|---|---|
| 8,062,252 B2* | 11/2011 | Alheidt | A61M 5/326 604/110 |
| 9,962,497 B2* | 5/2018 | Takemoto | A61M 5/3213 |
| 2003/0212380 A1* | 11/2003 | Barrelle | A61M 5/326 604/506 |
| 2007/0186510 A1 | 8/2007 | Wittland et al. | |
| 2018/0110934 A1 | 4/2018 | Wittland et al. | |
| 2018/0133409 A1 | 5/2018 | Fraas et al. | |
| 2018/0161511 A1 | 6/2018 | Fraas et al. | |
| 2018/0161512 A1 | 6/2018 | Wittland et al. | |
| 2018/0161516 A1 | 6/2018 | Wittland et al. | |

FOREIGN PATENT DOCUMENTS

| | | |
|---|---|---|
| CN | 102036705 A | 4/2011 |
| CN | 104619366 A | 5/2015 |
| DE | 29820166 U1 | 3/1999 |
| EP | 1 818 069 A1 | 8/2007 |
| EP | 3 106 188 A1 | 12/2016 |
| JP | 2018-517470 A | 7/2018 |
| WO | WO 1992/009319 A1 | 6/1992 |
| WO | 2009/137845 | 11/2009 |
| WO | WO 2011/110872 A1 | 9/2011 |
| WO | 2015/022787 | 2/2015 |

OTHER PUBLICATIONS

Canadian First Office Action, dated Oct. 18, 2018, in Canadian Patent Application No. 2,985,410, a related application, 1 pp.
International Search Report with Written Opinion corresponding to International Patent Application No. PCT/EP2016/060857, dated Aug. 18, 2016.
Indian Office Action, dated Aug. 30, 2019, in Indian Patent Application No. 201727040470, 3 pp.
Chinese First Office Action with English translation, dated Nov. 5, 2019, in Chinese Patent Application No. 201680027587.2, 15 pp.

* cited by examiner

SAFETY DEVICE FOR PREFILLED SYRINGES, COMPRISING AN ANTI-TRIGGERING MECHANISM

CROSS-REFERENCE TO RELATED APPLICATIONS

This application is a U.S. National Stage Application filed under 35 U.S.C. § 371 of International Application No. PCT/EP2016/060857, filed May 13, 2016, which claims the benefit of European Application No. EP15172166.9, filed Jun. 15, 2015. Both of these applications are hereby incorporated by reference in their entireties.

DESCRIPTION

The invention relates to a method for mounting a safety device and for mounting the safety device on a syringe body.

Until now, safety devices for avoiding stab wounds have been known in the art, which are mounted so as to surround the entire syringe once the syringes have been filled, for example by a supplier, under cleanroom conditions in a syringe nest or the like.

However, these safety devices increase the dimensions, in terms of both the sheer size and the weight of the syringe to be used, so that syringes having safety devices of this type are considerably more difficult to handle. Furthermore, the costs are also increased as a result of the greater amount of material used, as is the production time for a syringe comprising a safety device, since the safety device has to be assembled on the syringe in several steps.

Furthermore, such a structure of the safety device does not make it possible to mount the syringe in a syringe nest together with the safety device and to fill it therein, since the syringe nest corresponds to a DIN standard and therefore has a standardised size. Therefore, the syringe first has to be filled before it can be provided with the safety device. This of course also runs the risk of a person injecting themselves with a medicinal product that has been poured into the syringe.

Furthermore, subsequently attaching said safety device is disadvantageous in that the syringe that has already been filled can be damaged when mounting the safety device on the syringe, and is therefore unusable. This occurs in particular when the syringe is made of glass or another fragile material. If the syringe is damaged, the medicinal product contained therein is no longer useable either, which may lead to increased production costs.

The problem addressed by the present application is therefore that of providing a method for mounting a safety device so that the safety device can be mounted on the syringe body before the syringe body is filled, in particular so that said safety device can be mounted on the syringe body in a single step.

This problem addressed is solved by a method for mounting a safety device and for mounting the safety device on a syringe body before it is filled, comprising the steps of: providing a sleeve, a spring element and a mounting element; inserting the spring element into the interior of the sleeve in a mounting direction; inserting the mounting element into the interior of the sleeve along the mounting direction; obtaining the safety device; and mounting the safety device on the syringe body before the syringe body is filled by connecting the mounting element to the syringe body.

According to the invention, as in the present case, the safety device is therefore first assembled from a plurality of individual parts, specifically the sleeve, the spring element and the mounting element, and then mounted on the syringe body in a single step as a unit, in this case by connecting the mounting element to the syringe body.

In this case, the mounting direction extends from a proximal end of the sleeve towards a distal end of the sleeve. The spring element and the mounting element are therefore inserted at the proximal end of the sleeve and pushed towards the distal end, a bearing region preferably being arranged inside the sleeve, to which region at least the spring element is operatively connected by introducing said spring element into the interior of the sleeve, said element thus resting against the bearing region.

In a similar manner to the spring element, the mounting element is inserted into the interior of the sleeve. In this case, the mounting element can preferably be connected to the sleeve so that the spring element is held in the sleeve by the bearing region on one side and by the mounting element on the other side. The spring element is therefore secured such that it cannot fall out of the sleeve.

If a user of the syringe now moves the syringe body relative to the safety device, the spring element counteracts said movement and, if the relative movement is suppressed, would move the syringe body back again relative to the safety device.

The spring element can therefore ensure that the needle is securely moved back into the safety device, preferably automatically, after the syringe has been used. In this case, the spring element can have various designs. The spring element is preferably a spiral spring.

According to a preferred embodiment, the mounting element is connected to the syringe body by placing the mounting element on the syringe body.

According to a further preferred embodiment, the mounting element is clipped onto the syringe body, thus ensuring especially simple and secure mounting of the safety device on the syringe body.

For the mounting process, the mounting element preferably comprises a mounting opening, in which one or more latching elements may be arranged in order to clip the mounting element, and thus the safety device, onto said syringe body.

According to a preferred embodiment, the mounting element is connected to the sleeve by means of at least one guide pin, the guide pin advantageously being arranged on the mounting element.

In this case, the sleeve particularly advantageously comprises one or more recesses that form a guide track, the guide pin preferably being inserted into the recess or the guide track and the mounting element therefore being connected to the sleeve. When the syringe body is moved relative to the safety device, the guide pin can be guided by the guide track. For this purpose, it is advantageous for the mounting element to be able to move radially, i.e. to be able to rotate about an axis of the syringe body, but unable to move in the axial direction. This is achieved by clipping the mounting element onto the syringe body, for example, as described above.

The mounting element can particularly advantageously be inserted into the sleeve if said mounting element comprises sloping edges and/or cut-outs in which the guide pin is guided. The sleeve advantageously comprises a guide track in the form of a recess, in which the guide pin is introduced and therefore connects the sleeve and the mounting element to one another. The sloping edge and/or cut-out is therefore suitable for inserting the guide pin of the mounting element into the interior of the sleeve in a guided manner, thus making it easier and quicker to mount the safety device.

The safety device can be made even safer if an assembly comprising a cap and a needle guard is provided in addition to the sleeve, the spring element and the mounting element. This assembly allows the piercing element, for example a needle, to be guarded more effectively, in particular before the syringe is used for an injection. The assembly can advantageously be removed from the sleeve before the syringe is used.

According to a preferred embodiment, the assembly is connected to the sleeve by pushing the cap onto the sleeve counter to the mounting device, thus ensuring particularly simple and rapid mounting of the assembly on the sleeve.

The sleeve advantageously comprises recesses, which are complementary to the cap of the assembly so that a non-positive connection can thereby already be established by pushing to the cap onto the sleeve.

According to a further preferred embodiment, the syringe body together with the safety device mounted thereon is sterilised. Therefore, by mounting the safety device on the syringe body in advance, the entire arrangement can be sterilised in one step, as a result of which there is no need for several sterilisation steps, as is the case in the prior art as a result of subsequently mounting the safety device, and these steps can be omitted, thus reducing the production speed for a syringe and the system complexity.

According to another preferred embodiment, the syringe body together with the safety device mounted thereon is mounted in a syringe nest. The syringe nest comprising the syringe body together with the safety device is preferably mounted in a trough so that the syringe nest can be transported securely, for example to a company that fills the syringes. In this case, it is also possible to seal the trough comprising the syringe nest and syringe, preferably under cleanroom conditions, by means of a cover, for example a film.

Additional advantageous embodiments can be found in the dependent claims.

Additional aims, advantages and expediencies of the present invention can be found in the following description in conjunction with the drawings, in which.

Figure 1:
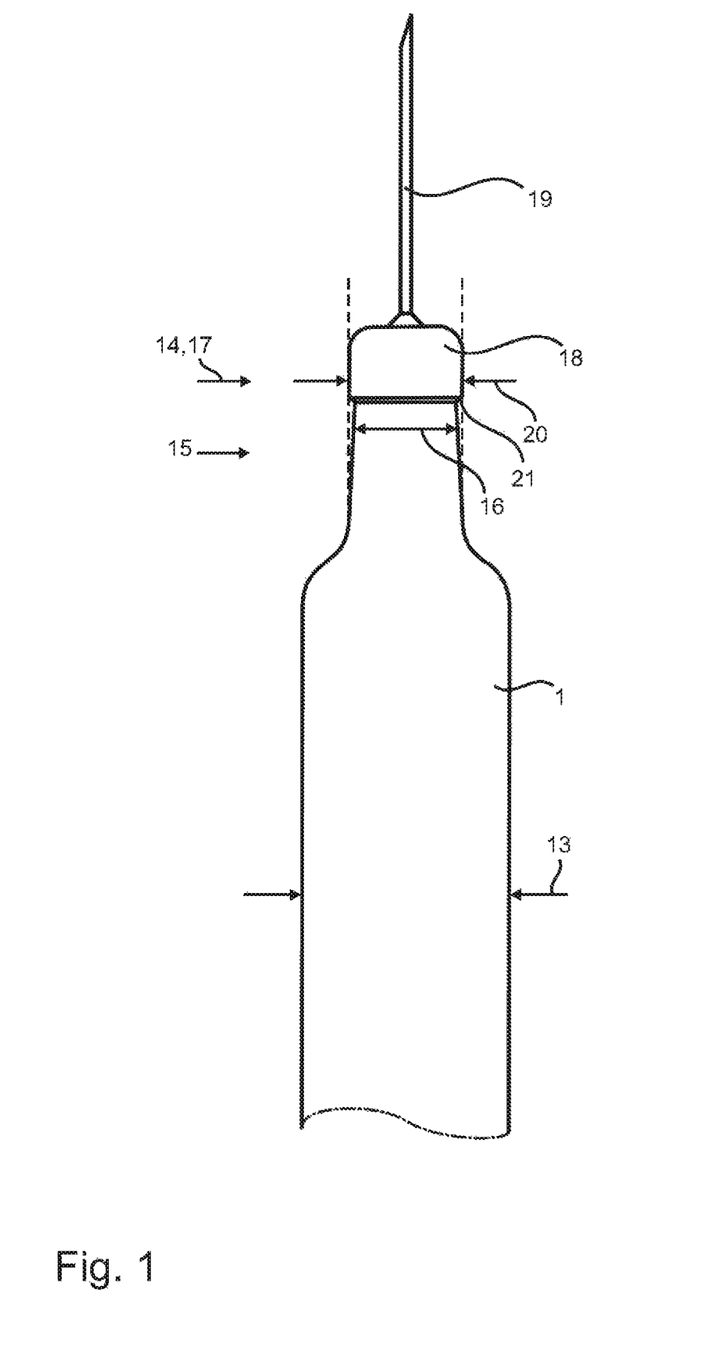
FIG. 1 shows a detail of the syringe body.

FIG. 1 shows a possible syringe body 1 that forms the basis of the invention. Commercially available syringe bodies 1 are substantially cylindrical, as is the syringe body 1 in the present case, and have a predetermined or predeterminable diameter 13. In this case, the syringe body 1 also comprises a narrower region 15 at its distal end 14, which is also substantially cylindrical. In this case, however, the narrower region 15 is in the shape of a truncated cone, the truncated-cone-shaped narrower region 15 having a diameter 16 at the cover surface (not shown here), i.e. the distal end 17 of the narrower region 15, the diameter 16 of the narrower region 15 being smaller than the diameter 13 of the syringe body 1.

Furthermore, in this case a needle holder 18 having a piercing element 19, a needle 19 in this case, is arranged at the distal end 17 of the narrower region 15, said needle holder 18 having a diameter 20 that is greater than the diameter 16 of the narrower region 15 but smaller than the diameter 13 of the syringe body 1. Furthermore, the needle holder 18 is arranged at the distal end 17 of the narrower region 15 such that a transition region 21 is formed, the transition region 21 forming a region in which the diameter 16 of the narrower region 15 and the diameter 20 of the needle holder meet one another and the diameter is thus intrinsically dramatically changed. The transition region 21 thus forms a type of projection.

Figure 2A:
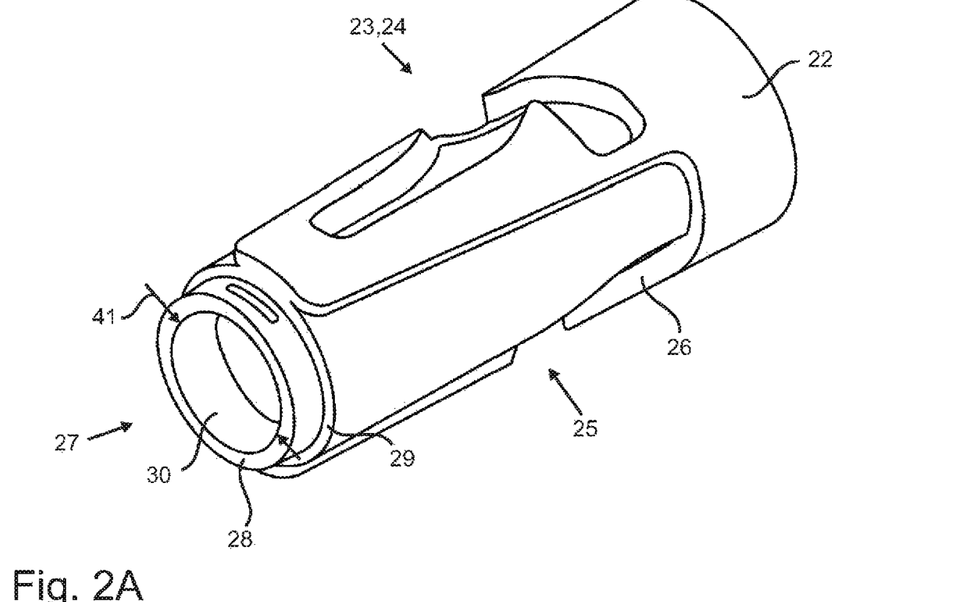
FIG. 2A is a perspective view of the sleeve from the front.

FIG. 2A is a perspective view of a first important component of the safety device 2, specifically the sleeve 22. As can be seen clearly from FIG. 2A, the sleeve comprises a recess 24, which forms the guide track 23 for guiding the guide pin 7 (not shown in this case). In addition, the sleeve 22 can comprise a recessed region 25, which is delimited by an edge 26. A mirror-image recess 24' is advantageously arranged opposite the recess 24 in the sleeve 22 and a mirror-image recessed region 25' is advantageously arranged opposite the recessed region 25 on said sleeve.

In this case, the recessed region 25 allows a cap 9 (see FIG. 2C) to be attached in a guided manner in order to increase the safety of the safety device 2. The cap 9 is at least in operative contact with and preferably at least non-positively connected to the sleeve 22 by means of the edge 26 of the recessed region 25.

Furthermore, the sleeve 22 comprises an annulus 28 and an annular region 29 at its distal end 27, which is arranged so as to surround the annulus 28 when viewed in the radial direction. The cap 9 is placed on the annulus 28 such that, in addition to being non-positively connected to the recessed region 25, the cap 9 is additionally non-positively connected to the sleeve 22.

Figure 2B:
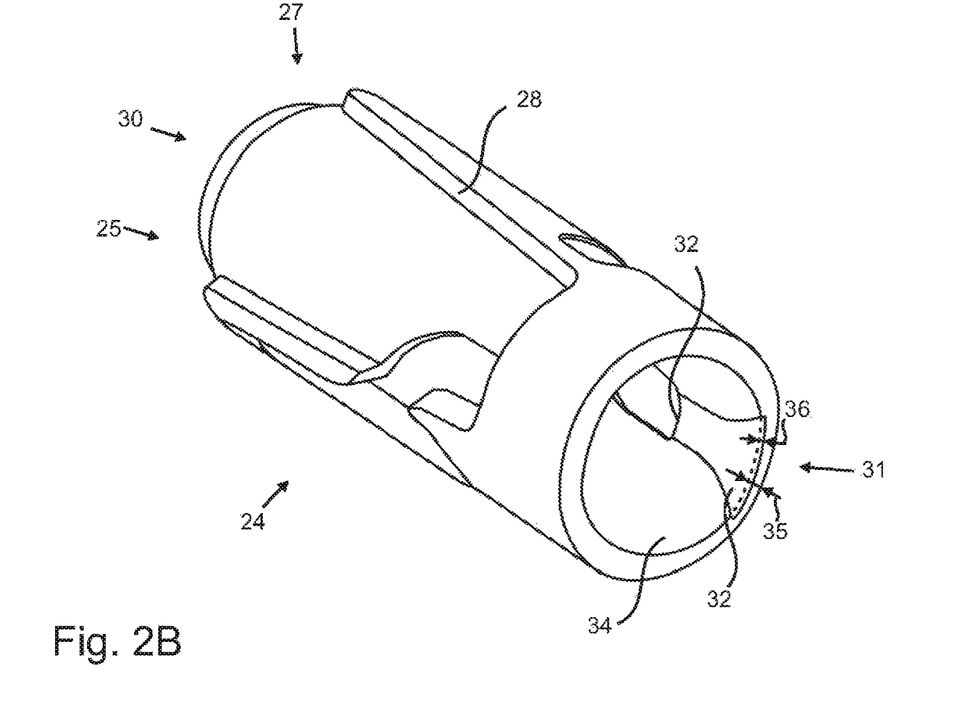
FIG. 2B is a perspective view of the sleeve from behind.

FIG. 2B once again shows the sleeve 22, but from a different perspective to that in FIG. 2A. FIG. 2B shows in particular the proximal end 31 of the sleeve 22, which comprises at least one slanting portion 32. The number of slanting portions 32 is preferably equal to the number of guide pins 7, and said portions are formed on the sleeve 22 so as to be complementary to the guide pins 7.

The slanting portions 32 constitute a guide for the guide pins 7 when the safety device 2 is assembled, the slanting portions constituting a depression in the inner wall 34 of the sleeve so that the wall thickness 35 of the sleeve 22 has been reduced by the magnitude 36 of the depression 32, making it easier to introduce the mounting element 5, in particular to introduce the guide pin 7, into the sleeve 22.

Figure 2C:
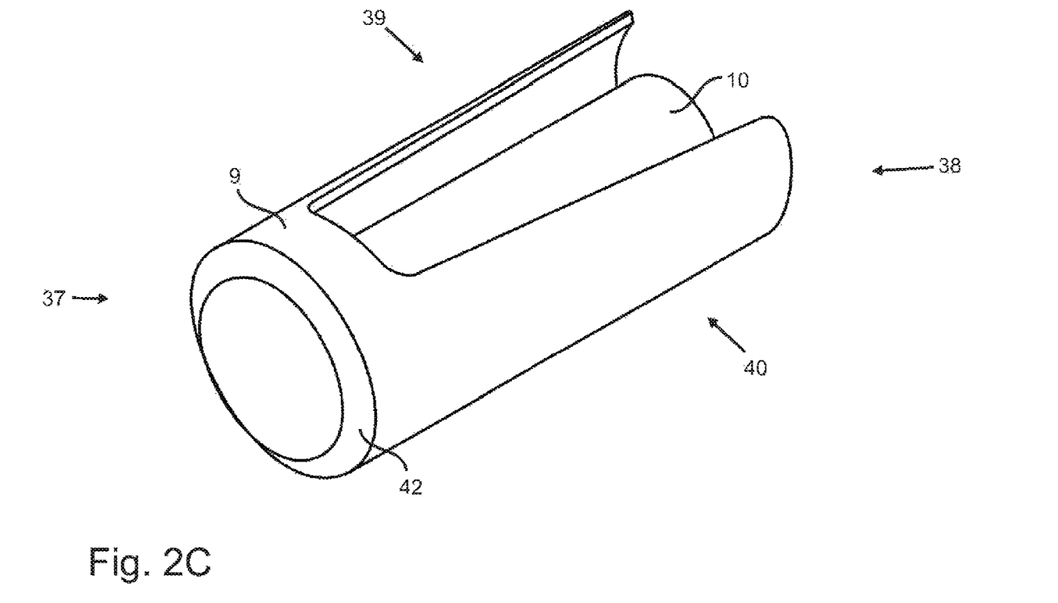
FIG. 2C is a perspective view of the cap.

FIG. 2C shows a cap 9, on which a needle guard 10 is likewise arranged. In this case, the cap 9 comprises a first wing element 39 and a second wing element 40, which are designed to be complementary to the recessed regions 25. In this case, the external diameter (not shown here) of the needle guard 10 is smaller than the internal diameter 41 of the exit opening 30 or of the sleeve 22, thus ensuring that the needle guard 10 can be inserted into the sleeve 22.

Figure 2D:
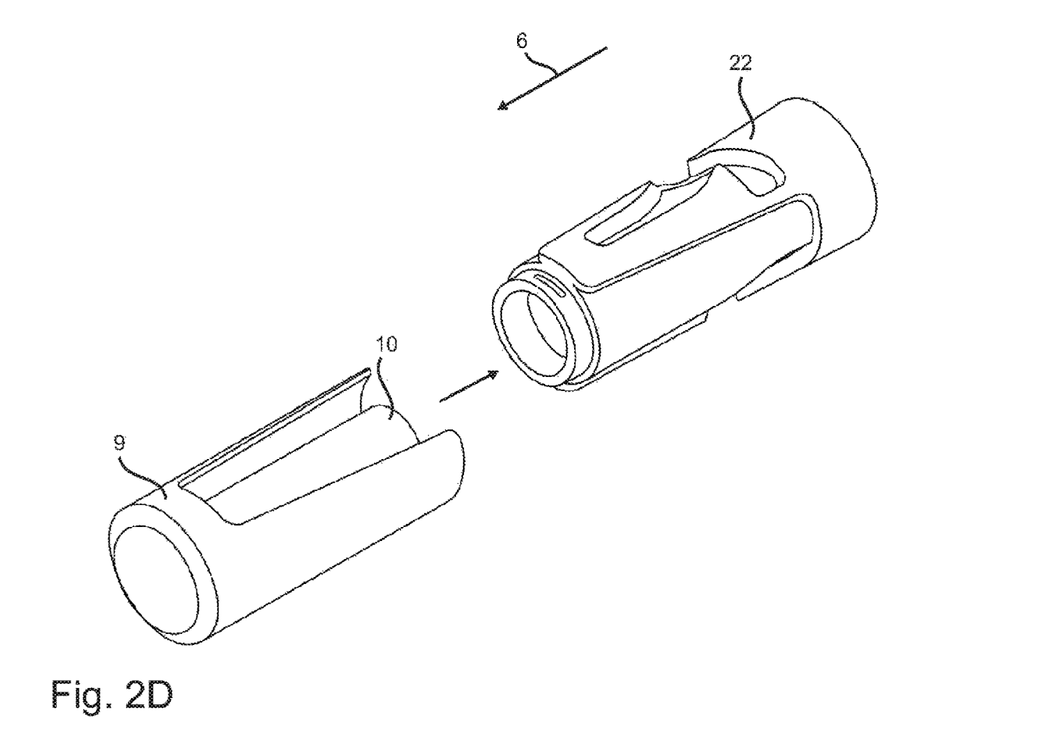
FIG. 2D shows the cap being mounted onto the sleeve.

In the present case, FIG. 2D shows how the cap 9 and the needle guard 10 are pushed onto the sleeve 22 counter to the mounting direction 6, which extends from the proximal end 31 of the sleeve to the distal end 27 along a longitudinal direction of the sleeve 22. Following mounting, an annular region 42 of the cap 9 is preferably in contact with the annulus 28. However, it is also conceivable for the annular region 42 to be in contact with the annular region 29.

Figure 3A:
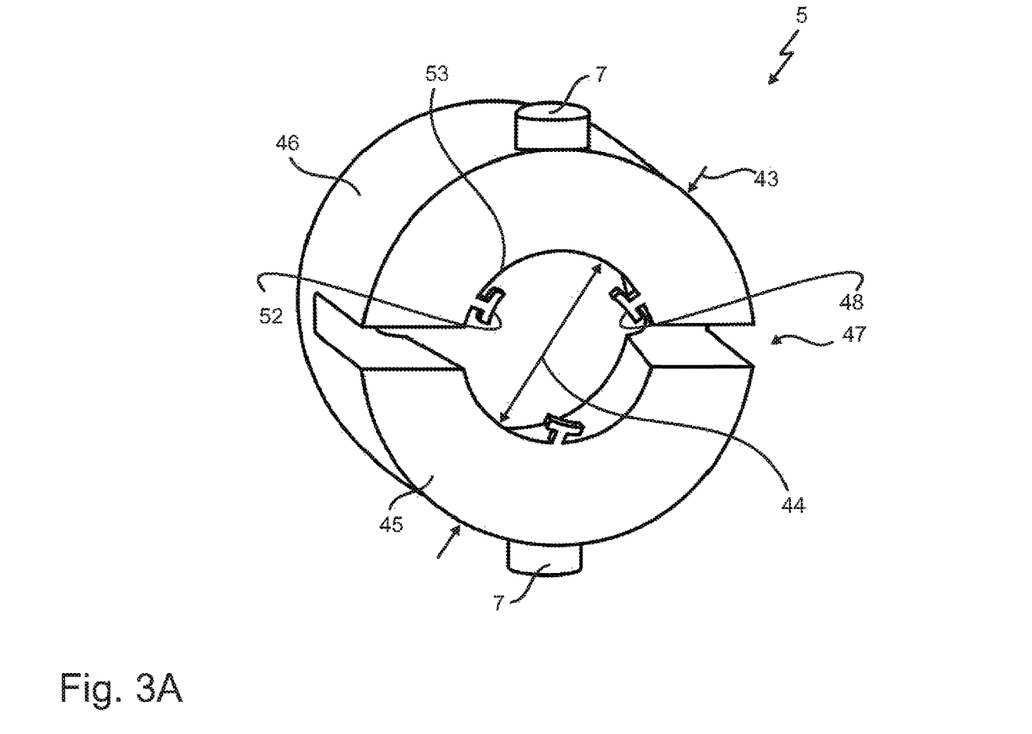
FIG. 3A is a perspective view of the mounting element from above.
Figure 3B:
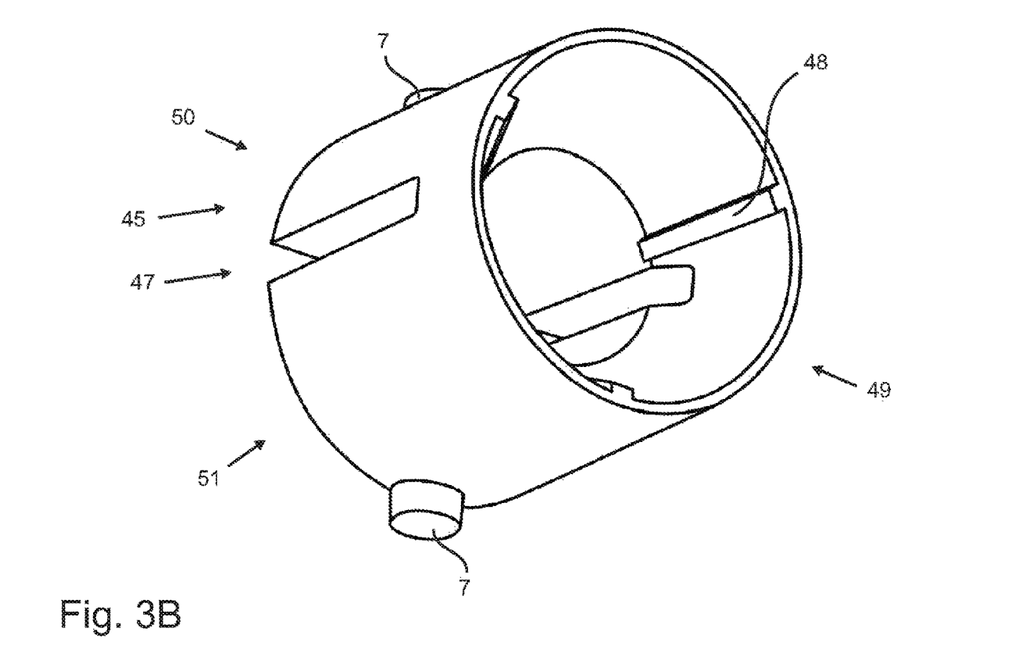
FIG. 3B is a perspective view of the mounting element from below.

FIGS. 3A and 3B show the mounting element 5, by means of which the sleeve 2 and therefore the safety device 2 can be connected to the syringe body 1 as a whole, FIG. 3A being a perspective view from above of the mounting element 5 and FIG. 3B being a perspective view from below of the mounting element 5.

The mounting element 5 is substantially cylindrical in this case, having an external diameter 43 and an internal diameter 44. Reference numeral 45 denotes the distal end of the mounting element 5.

In this case, two guide pins 7 are arranged on a lateral face 46 of the mounting element 5, which lie on opposite sides of the mounting element 5. Said guide pins 7 can then be arranged in the guide track 23 of the sleeve and be operatively connected thereto.

In addition, the mounting element 5 comprises one or more, in this case two, cut-outs 47 and one or more, in this case three, latching elements 48, the function of which is outlined below with reference to FIG. 3B.

In FIG. 3B, reference numeral 49 denotes a proximal end 49 of the mounting element 5. As can be seen, the latching elements 48 of the mounting element 5 extend so as to increase in size from the proximal end 49 towards the distal end 45, i.e. the latching elements 48 are larger at the distal end 45 than at the proximal end 49 when viewed in the radial direction.

If, when joining the mounting element 5 and the syringe body 1, in particular the narrower region 15 thereof, the mounting element 5 is first pushed onto the needle holder 18 by its proximal end 49, a first half 50 and a second half 51 of the mounting element 5, which are separated by the cut-outs 47, are moved away from one another as a result of the difference in thickness in the radial direction that increases in the axial direction. It is therefore necessary here for the mounting element 5 to be at least partially resilient.

If the distal end 45 of the mounting element 5 passes the transition region 21, the first 50 and the second 51 halves move towards one another as a result of the resilient design, so that the mounting element 5 and therefore the safety device 2 are ultimately clipped onto the syringe body 1.

In order to secure this clip connection, the latching elements 48 comprise securing portions 52 at their distal end 45, which portions extend in the circumferential direction of an inner circle 53 of the mounting element 5 and are mechanically operatively connected to the transition region 21.

The safety device 2 comprising the sleeve 2, the mounting element 5, the spring element 4 and optionally the cap 9 can particularly preferably be mounted in advance and can be connected to the syringe body 1 as a whole by means of the mounting element 5.

Figure 4:
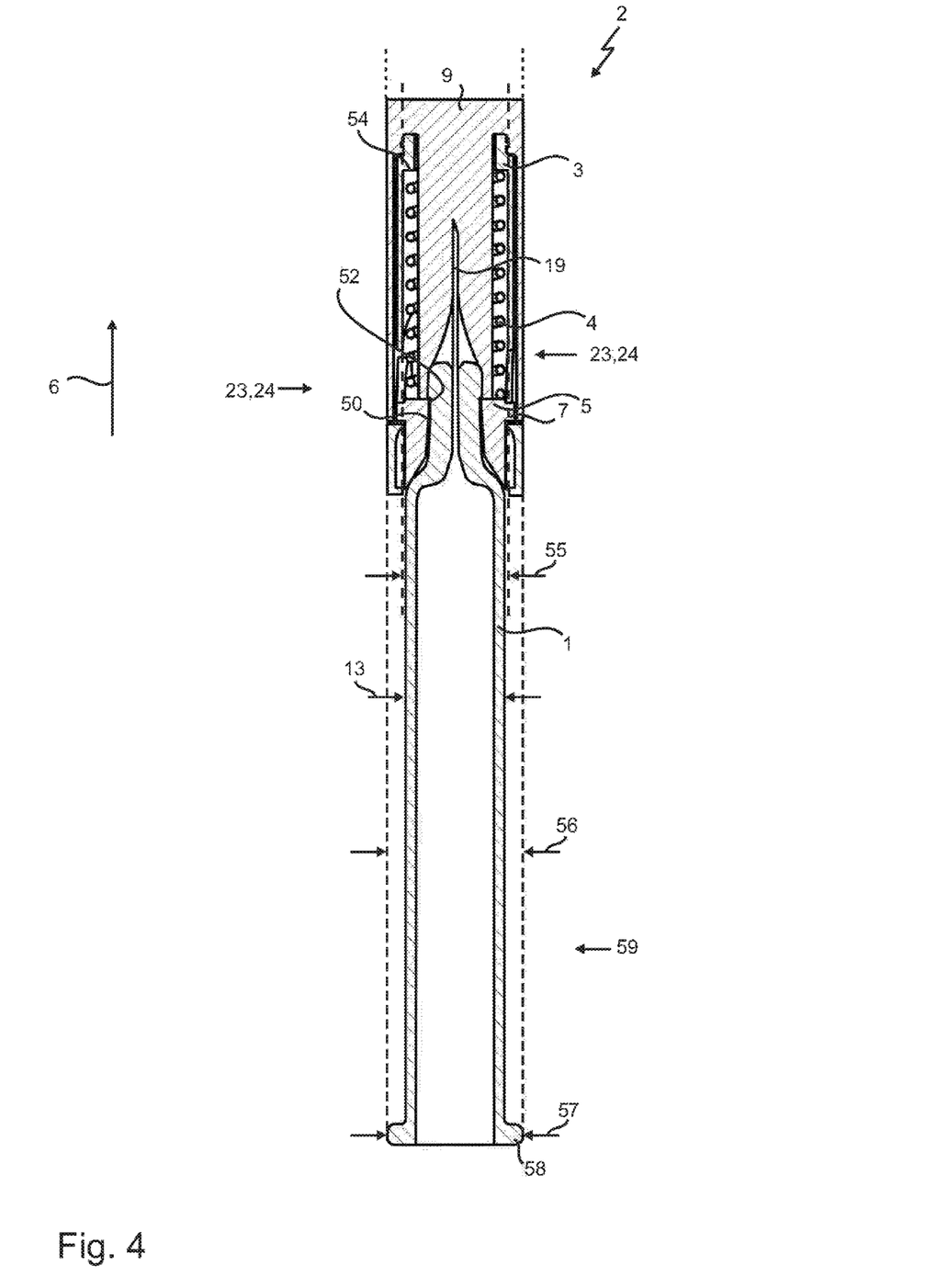
FIG. 4 is a longitudinal section of a syringe body comprising the safety device mounted thereon.

FIG. 4 is a longitudinal section of a syringe body 1 comprising a safety device 2 mounted thereon.

In addition to the cap 9, the sleeve 22 and the mounting element 5, the safety device 2 now also features the spring element 4, which is formed as a spiral spring 4 in this case.

As can clearly be seen, the guide pins 7 are in contact with the recess 24 or the guide track 23, so that the guide pins 7 are guided by the guide track 23 when the syringe body 1 is moved relative to the safety device 2.

The mounting element 5 is clipped together with the narrower region 15 by means of the latching elements 48 and the securing portions 52 thereof, and is connected to the sleeve 22 by means of the guide pins 7.

The sleeve 22 also comprises an internal bearing region 54 at its distal end 27, which can be operatively connected to the spring element 4. The spring element 4 is therefore held in the sleeve 22 by the bearing region 54 on one side and by the mounting element 5 on the other side, and is therefore secured against falling out.

The safety device 2 is dimensioned such that the sleeve 22 has an internal diameter 55 that is greater than the diameter 13 of the syringe body 1, and therefore the syringe body 1 can be moved into the sleeve 22 when it is moved forwards in the longitudinal direction L, the movement direction being shown by an arrow L, relative to the safety device 2. At the same time, the external diameter 56 of the sleeve 22 or of the safety device 2 is selected so as to correspond to no greater than a maximum diameter 57 of a retaining apparatus 58, attached to the proximal end 59 of the syringe body 1, for retaining and securely positioning the syringe. The purpose of this size restriction is explained in more detail with reference to FIGS. 5 and 6.

Figure 5:
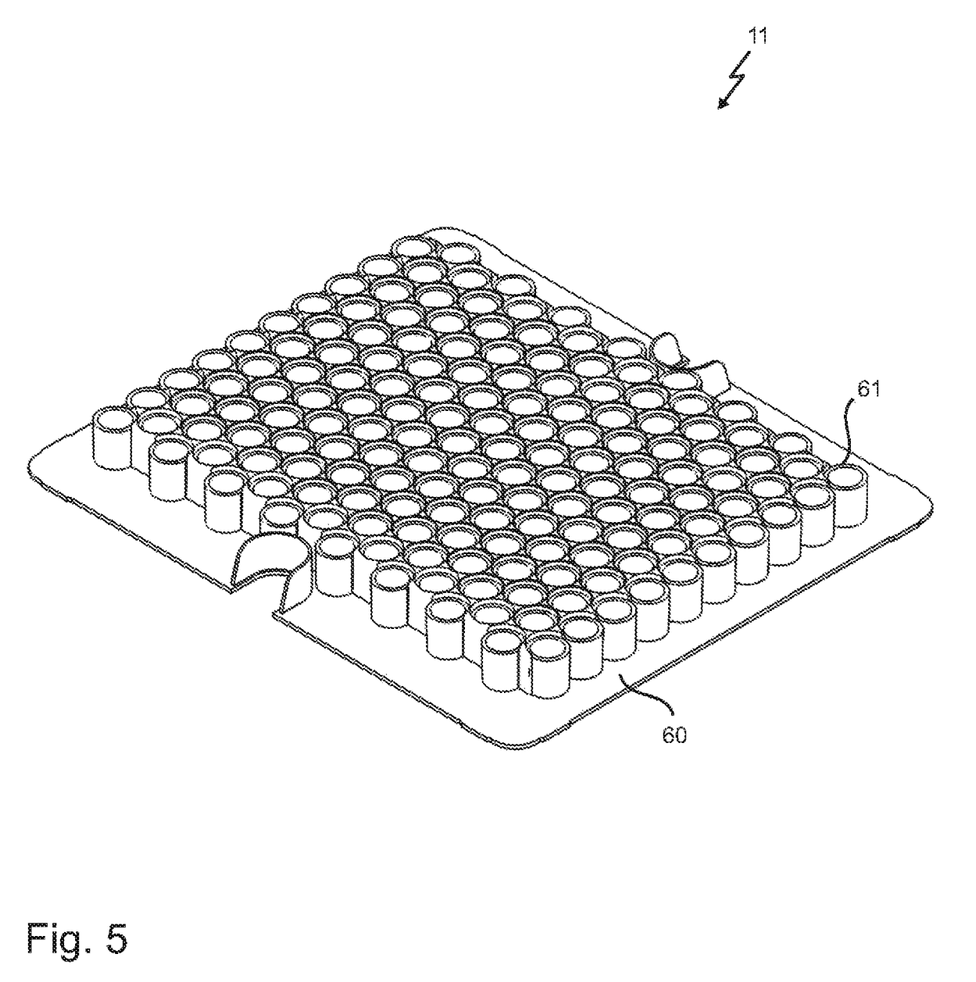
FIG. 5 shows a syringe nest.

FIG. 5 shows a syringe nest, as already known in the art, comprising a base plate 60, on which there are arranged hollow cylinders 61, i.e. in particular openings 61, in which the syringes can be mounted. In this case, the base plate 60 is used to fasten the syringe nest in a trough 12 (not shown in this case).

Figure 6:
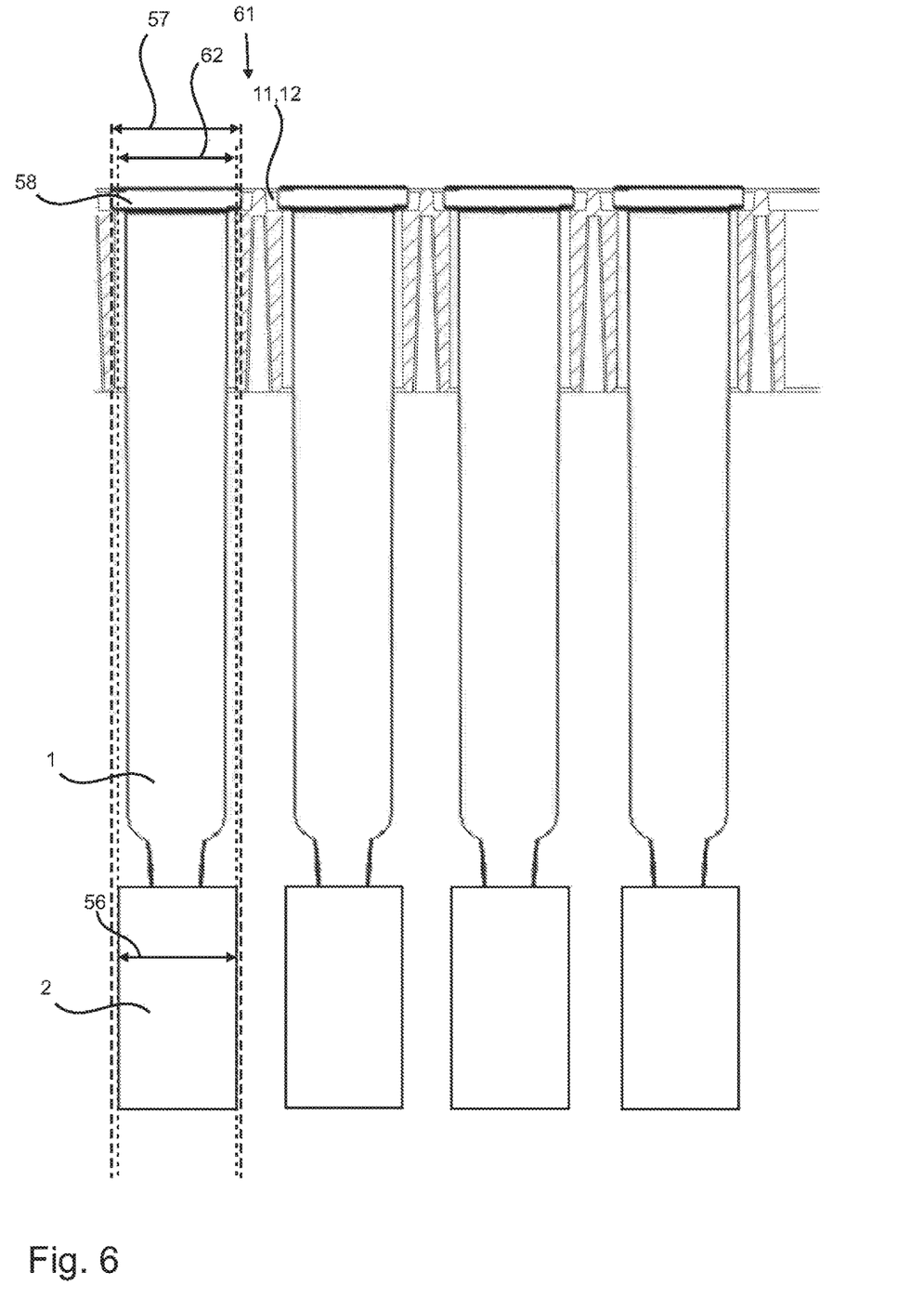
FIG. 6 shows syringes mounted in a syringe nest, comprising a syringe body and a safety device.

For this purpose, FIG. 6 shows a detail of a longitudinal section of a syringe nest 11 comprising syringes mounted therein, the syringes comprising a syringe body 1 and a safety device 2. In this case, the syringe body 1 has been mounted in the syringe nest together with the safety device 2. In order to be able to mount a syringe in the syringe nest 11, the diameter 57 of the retaining apparatus 58 is selected to be greater than the diameter 62 of an opening 61. In order to be able to mount the syringe body 1 together with the safety device 2 in an opening 61, the external diameter 56 of the sleeve 22 and the external diameter 56 of the safety device 2 therefore have to be selected to be smaller than the diameter 57 of the retaining apparatus 58. It is therefore possible to already mount the syringe in the syringe nest together with the safety device 2, and to sterilise and fill it therein.

The syringe nest 11 comprising the syringe body 1, the syringe nest 11 being mounted in the trough 12, can then be sealed and/or closed by means of a cover, in particular a film and/or a membrane. The film is, for example, made of plastics material and the membrane is a Tyvek film. Once the trough 12 has been sealed and/or closed, the arrangement in the present case is sterilised.

Figure 7:
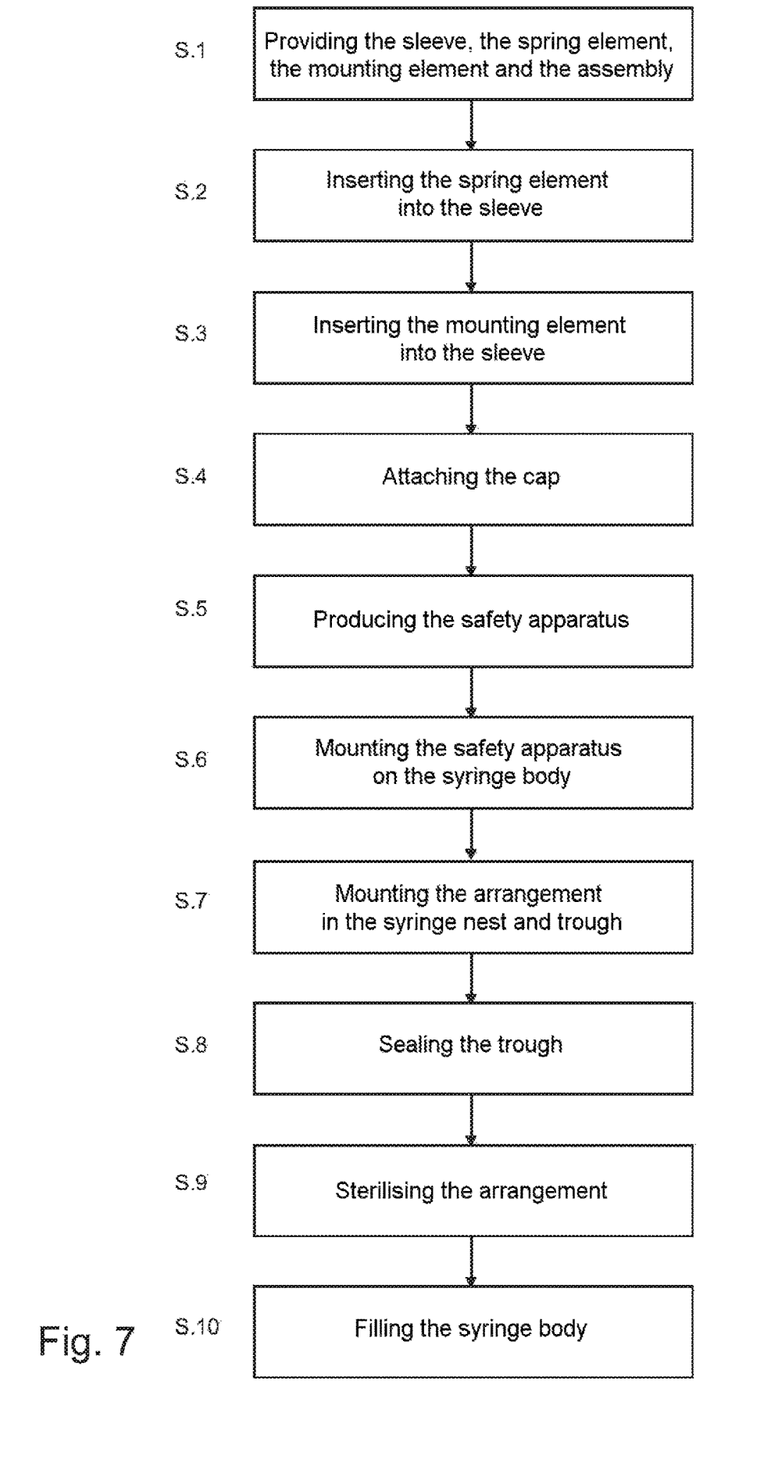
FIG. 7 is a flow diagram showing the individual method steps according to one embodiment.

FIG. 7 depicts a method sequence according to a particularly preferred embodiment.

In a first step, step S.1, the respective elements, the sleeve 3, the spring element 4, the mounting element 5 and the assembly 8 comprising the cap 9 and the needle guard 10 are provided. These elements are preferably prefabricated components, which are mass-produced.

In step S.2, the spring element 4 is inserted into the interior of the sleeve 3 and is secured against falling out by the mounting element 5 being inserted into the interior of the sleeve 3 in step S.3.

In a subsequent step, step S.4, onto the sleeve 3 an assembly 8, in particular the cap 9, is pushed onto the sleeve 3 so that the safety device 2 is mounted in advance and obtained in step S.5.

The safety device 2 obtained is mounted on the syringe body 1 in a single step in step S.6 by the safety device 2 being pushed onto the distal end of the syringe body 1 and the mounting element 5 therefore being connected to the syringe body 1.

Once the safety device 2 has been mounted on the syringe body 1, the entire arrangement can be mounted in a syringe nest 11 and a trough 12 in step S.7, and in step S.8 the trough 12 can be sealed, for example by means of a protective film and/or a membrane, preferably a Tyvek film.

In a subsequent step, step S.9, the arrangement consisting of the syringe body 1 comprising the safety device 2 and the trough 12 comprising the syringe nest 11 is sterilised, preferably under cleanroom conditions.

In a final step, step S.10, the film is preferably removed again so that the syringe body 1 can be filled. In a subsequent step (not shown), the syringe bodies 1 that have been filled are provided with stoppers or the like and thus sealed and then placed in commercially available packaging.

All of the features disclosed in the application documents are claimed to be essential to the invention provided that they are novel over the prior art, either on their own or in combination with one another.

LIST OF REFERENCE NUMERALS 1 syringe body
2 safety device
3 sleeve
4 spring element
5 mounting element
6 mounting direction
7 guide pin
8 assembly
9 cap
10 needle guard
11 syringe nest
12 trough
13 diameter of the syringe body
14 distal end of the syringe body
15 narrower region
16 diameter of the narrower region
17 distal end of the narrower region
18 needle holder
19 piercing element
20 diameter of the needle holder
21 transition region
22 sleeve
23 guide track
24 recess
25 recessed region
26 edge
27 distal end of the sleeve
28 annulus
29 annular region
30 exit opening
31 proximal end of the sleeve
32 slanting portion
33 transition
34 inner wall of the sleeve
35 wall thickness
36 magnitude of the depression
37 distal end of the cap
38 proximal end of the cap
39 first wing element
40 second wing element
41 internal diameter
42 circular edge
43 external diameter of the mounting element
44 internal diameter of the mounting element
45 distal end of the mounting element
46 lateral face
47 cut-out
48 latching element
49 proximal end of the mounting element
50 first half
51 second half
52 securing portion
53 inner circle
54 bearing region
55 internal diameter of the sleeve
56 external diameter of the sleeve
57 maximum diameter
58 retaining apparatus
59 proximal end of the syringe body
60 base plate
61 opening
62 diameter of the opening

The invention claimed is:

1. A method for mounting a safety device on a syringe body before the syringe body is filled, comprising the steps of:
   a. assembling a safety device comprising a sleeve, a spring element and a mounting element, wherein assembling the safety device comprises the steps of:
      i. providing the sleeve, the spring element and the mounting element,
      ii. inserting the spring element into the interior of the sleeve along a mounting direction, and
      iii. inserting the mounting element into the interior of the sleeve along the mounting direction, thereby assembling the safety device,
   b. mounting the safety device on the syringe body before the syringe body is filled by connecting the mounting element to the syringe body, and
   c. mounting the syringe body together with the safety device mounted thereon in a syringe nest for subsequent filling of the syringe body,
   wherein at least one guide pin is arranged on the mounting element, and the sleeve comprises at least one recess, which forms a guide track for guiding the guide pin, and at least one slanting portion at a proximal end, which constitutes a depression in an inner wall of the sleeve and is complementary to the at least one guide pin, and
   wherein in step iii., the mounting element is connected to the sleeve by means of the at least one guide pin, the guide pin being guided by the slanting portion and by the guide track,
   wherein the safety device is first assembled and then mounted on the syringe body in a single step as a unit.

2. The method according to claim 1, wherein the mounting element is connected to the syringe body by the mounting element being placed on the syringe body.

3. The method according to claim 2, wherein the mounting element is clipped onto the syringe body.

4. The method according to claim 1, further comprising an assembly comprising a cap and a needle guard.

5. The method according to claim 4, wherein the assembly is connected to the sleeve by pushing the cap onto the sleeve counter to the mounting direction.

6. The method according to claim 1, wherein the syringe body together with the safety device mounted thereon are sterilised.

7. The method according to claim 1, wherein the syringe nest is mounted in a trough.

\* \* \* \* \*

(12) SUPPLEMENTAL EXAMINATION CERTIFICATE

United States Patent
Wittland et al.

(10) Number: US 10,682,472 F1
(45) Certificate Issued: Apr. 7, 2021

Control No.: 96/000,352

Filing Date: Mar. 23, 2021

Primary Examiner: William C. Doerrler

No substantial new question of patentability is raised in the request for supplemental examination. See the Reasons for Substantial New Question of Patentability Determination in the file of this proceeding.

(56) Items of Information

FOREIGN PATENT DOCUMENTS

| | | |
|---|---|---|
| DE | 29820166 U1 | 03/25/1999 |
| EP | 1818069 A1 | 08/15/2007 |
| WO | 2011/110872 A1 | 09/15/2011 |